United States Patent
Li et al.

(10) Patent No.: US 9,342,398 B2
(45) Date of Patent: May 17, 2016

(54) CT SCANNING SYSTEM AND A METHOD FOR RECEIVING AND TRANSMITTING RAW DATA THEREIN

(71) Applicant: GE MEDICAL SYSTEMS GLOBAL TECHNOLOGY COMPANY, LLC, Waukesha, WI (US)

(72) Inventors: Qinglei Li, Beijing (CN); Guowang Li, Beijing (CN); Xiaoran Dong, Beijing (CN)

(73) Assignee: GE MEDICAL SYSTEMS GLOBAL TECHNOLOGY COMPANY, LLC, Waukesha, WI (US)

(*) Notice: Subject to any disclaimer, the term of this patent is extended or adjusted under 35 U.S.C. 154(b) by 138 days.

(21) Appl. No.: 14/166,992

(22) Filed: Jan. 29, 2014

(65) Prior Publication Data
US 2014/0215280 A1    Jul. 31, 2014

(30) Foreign Application Priority Data
Jan. 31, 2013   (CN) .......................... 2013 1 0037980

(51) Int. Cl.
G06F 11/00   (2006.01)
G06F 11/08   (2006.01)
A61B 6/03    (2006.01)
A61B 6/00    (2006.01)
H04L 1/18    (2006.01)

(52) U.S. Cl.
CPC .............. *G06F 11/08* (2013.01); *A61B 6/032* (2013.01); *A61B 6/56* (2013.01); *H04L 1/18* (2013.01)

(58) Field of Classification Search
CPC .......................... G06F 11/1469; G06F 11/1456
See application file for complete search history.

(56) References Cited

U.S. PATENT DOCUMENTS

| | | | | |
|---|---|---|---|---|
| 6,185,272 B1* | 2/2001 | Hiraoglu | ............ | G01V 5/0008 378/57 |
| 7,032,132 B2* | 4/2006 | Adachi | .......................... | 714/28 |
| 7,436,924 B2* | 10/2008 | Takahashi et al. | ................ | 378/4 |
| 2004/0116797 A1* | 6/2004 | Takahashi | ............... | A61B 6/032 600/407 |
| 2006/0083351 A1* | 4/2006 | Lamberty | ................ | A61B 6/00 378/86 |
| 2013/0198200 A1* | 8/2013 | Takei | ................ | G06F 17/30619 707/741 |
| 2014/0219416 A1* | 8/2014 | Kimoto | ................. | G06T 7/0081 378/8 |
| 2014/0350393 A1* | 11/2014 | Ichihara | ................. | A61B 5/029 600/425 |

FOREIGN PATENT DOCUMENTS

EP    1852996 A2    11/2007

* cited by examiner

*Primary Examiner* — Amine Riad
(74) *Attorney, Agent, or Firm* — GE Global Patent Operation

(57) ABSTRACT

A method of transmitting raw data by a data acquisition system in a CT scanning system, wherein the CT scanning system comprises a rotational part of a gantry with at least one raw data backup memory, and wherein the data acquisition system is configured to adopt the at least one backup memory for storing a backup of the raw data. The method comprising: generating the raw data as scanned; storing generated raw data in the at least one backup memory; transmitting the raw data to an operation console in the CT scanning system; and repeating generating, storing, and transmitting of the raw data in the case of an unfinished scan, until the unfinished scan is finished.

19 Claims, 6 Drawing Sheets

Flow Diagram Showing the Method of Transmitting Raw Data by the DAS of the Present Invention CT Scanning System Block Diagram X-Ray Tube and Data Detection-Acquisition Part Block Diagram X-Ray Tube and Data Detection-Acquisition Part Schematic Diagram Data Acquisition System Block Diagram Block Diagram of the CT Scanning System of the Present Invention Flow Diagram Showing the Method of Transmitting Raw Data by the DAS of the Present Invention

Flow Diagram Showing the Method of Receiving Raw Data by the OC of the Present Invention

Schematic Diagram of Data Echoplex and Signal Splitting of the Present Invention Schematic Diagram of Another Data Echoplex and Signal Splitting of the Present Invention

CT SCANNING SYSTEM AND A METHOD FOR RECEIVING AND TRANSMITTING RAW DATA THEREIN

TECHNICAL FIELD

The present invention relates to a Computed Tomography (CT) scanning system and a method for receiving and transmitting raw data therein.

BACKGROUND OF THE INVENTION

FIG. 1 shows schematically a block diagram of a CT scanning system; the block diagram is only showed by way of example, and persons skilled in the art can appreciate that, an actual CT scanning system may have more or less or different components as compared with the system shown in FIG. 1 according to different system configurations. It can be seen from FIG. 1 that, a CT scanning system is generally comprised of four subsystems: an operation console (OC), a gantry, a scanning table and a power distribution unit (PDU), wherein the gantry subsystem further comprises such components as a data-detection-acquisition part and an X-ray generator.

The operating overview of the CT scanning system will be described in connection with FIG. 1. The OC controls the entire system, according to the operator's operations. The OC sends instructions to the Table gantry Processor (TGP) board (the TGP board is a main controller of the scanning table/gantry subsystems) on the stationary part of the gantry, and the TGP board subsequently controls the gantry and the Scanning table according to some of these instructions. The TGP board passes some instructions of the OC to the On gantry Processor (OGP) board mounted on the rotational part of the gantry. According to the destinations of these instructions passed from the TGP board, the OGP board passes these instructions to such components as the Data Acquisition System (DAS), X-ray Generator, etc., respectively, such that the OC can control these components. The OC can also send an instruction whose destination is the OGP board, and this instruction is performed by the OGP board per se. Reversely, the OC receives status information from the TGP board or from other components (such as the OGP board) via the TGP board.

As shown in FIG. 1, the gantry can be divided into the stationary part and the rotational part, and the communication between the stationary part and the rotational part is realized by a slip ring; the slip ring is a rotational mechanism allowing exchange of power and signal, and the link on the slip ring for transmitting raw data is different from the link on the slip ring for communication between the OGP board and the OC (via the TGP board). The stationary part of the gantry is mainly controlled by the TGP board, and the TGP board is in communication with the OGP board via cables and the slip ring.

FIG. 2 is a block diagram of the X-ray tube and the data detection-acquisition part; FIG. 3 is schematic diagram of the X-ray tube and the data detection-acquisition part. The data detection-acquisition part consists of the DAS and a detector that are located on the rotational part of the gantry. X-ray data acquired by the detector is converted to light, then to electrical signals in the detector and then sent to the DAS. The DAS digitizes, serializes and performs offset correction on the signal and then sends it via the slip ring to the Operator Console for image reconstruction. In addition, persons skilled in the art understand that the detector can also be comprised in the DAS.

Specifically, the DAS can comprise CAM board, DDP board and CIF board, as shown in FIG. 4. The CIF board exchanges signals with the OGP board to control and synchronize the data acquisition, and generates control and timing signals to the other boards in the DAS. The CAM board converts electrical current that is generated by the detector and is proportional to the X-ray intensity to voltage signal. In the CAM board, the voltage signal is amplified to an appropriate level, converted to serial digital data, and then converted to parallel data. The offset correction of the data is performed in the DDP board. The data is then sent to a transmission preparation module. As known by persons skilled in the art, the transmission preparation module and the DAS are separate components in traditional CT scanning systems, and the existing CT scanning systems do not have a separated transmission preparation module, and integrate the functions of the transmission preparation module into the DAS instead. The CT scanning system of some embodiments of the present invention also integrate the functions of the transmission preparation module into the DAS without a separated transmission preparation module; the separation of the transmission preparation module from the DAS as shown in the drawings is only used to more conveniently explain the functions of the DAS.

The transmission preparation module performs the following preparation tasks of data transmission: FEC error correction code generation, parallel/serial conversion, view packing, and electric to light signal conversion. In the transmission preparation module, the FEC encoder adds error correction code to conduct error detection and error correction to the transmitted data in the OC; the optical transmitter converts the electric signal to light signal, which is sent to the RF transmitter by optical fiber. The RF transmitter transmits the signal to the RF receiver on the stationary part side of the gantry, and in the RF receiver, the signal is converted again to light signal and is transmitted by optical fiber to the DAS Interface (DASIF) in the OC. This interface converts the serial light signal raw data from the DAS into parallel electric signal raw data. The RF transmitter antenna and the RF receiver antenna are both located on the slip ring.

Data that is generated and transmitted by the DAS (including the transmission preparation module) is called raw data, so the transmitting path of raw data include the optical fiber from the DAS to the RF transmitter, the RF transmitter, the slip ring, the RF receiver, and the optical fiber from the RF receiver to the OC. If a failure occurs in any component on the transmitting path of raw data, a problem will occur in the transmission of raw data. Although the CT scanning system adds error correction codes when transmitting raw data, many data problems, such as missing data package, cannot be corrected by the error correction codes. In addition, the DAS does not store the backup of raw data in the rotational part of the gantry when transmitting raw data to the OC. This design does not provide any redundancy backup capacity for raw data, so it is very hard to avoid the following drawbacks.

When, e.g., the occasional problems of data are caused by interference sources (unexpected factors, such as voltage mutation or mobile phone signal interference near the gantry, etc.) that occasionally appear on the transmitting path of raw data or data receiving interface, and these problems cannot be corrected by error correction codes. The OC will remedy the problem of data package via the proper post-processing (e.g., interpolation scheme), but the image quality of reconstruction will be impacted by doing so. Moreover, when the number of data problems reaches a certain threshold, such that these data contain too many problems to be remedied by post-processing of image reconstruction, the OC will abort scanning. At that moment, the scanning object me be re-scanned because the data received and stored in the OC before the scanning is aborted cannot be used for image reconstruction due to containing too many problems. However, re-scanning will expose the scanning object to more radiation.

In the case of a serious failure, such as the transmitting path of raw data being damaged, soft/hardware invalidation on the OC, or power down of the OC, scanning will also be aborted. In this case, some data that is transmitted prior to the abortion of the scan, is missed due to the serious failures, such that the data received and stored in the OC before scanning is aborted is not intact, so the restoring scanning cannot be started from the point at which it is aborted, and the object being scanned must also be re-scanned.

Upon the completion of a scan, the rotational part of the gantry does not store the backup of raw data. In the on-site detection of failures in the transmitting path of raw data, the data that can be analyzed after the scan is complete is only the data containing problems that is stored in the OC, such that persons skilled in the art cannot quickly locate in which sections of the transmitting path of raw data failures appear, thereby leading to very low detection efficiency.

BRIEF SUMMARY OF THE INVENTION

Embodiments of the present invention avoid the above drawbacks of the existing scanning systems by placing on the rotational part of the gantry one or more raw data backup memories (hereinafter referred to as "backup memories") that are used by the DAS for accessing the backup of raw data. The raw rata backup stored in the backup memories provides higher system redundancy to the scanning system, such that the OC can adopt the raw data backup that is retransmitted from the backup memories to remedy the problems appearing in the received raw data so as to not affect the quality of the reconstructed image and not abort the scan. Some serious failures will not cause aborting of scanning because the backup memories can continually receive raw data. The DAS can also send a warning message to the OC by, e.g., comparing the transmitted raw data and the corresponding backup in the backup memories and find the inconsistency between the data and the corresponding backup, so as to facilitate failure detection, and to speed up the progress of on-site maintenance and engineering development. The CT scanning system can also be applied in areas or situations in which power supply is not stable, as long as the power supply still can maintain the normal operation of the rotational part of the gantry to enable the DAS to store raw data in the backup memories, even if the power supply is not sufficient to keep the normal operation of other parts of the CT scanning system including the OC, the scanning can thus still be continued. This means that an UPS device, which is generally provided by the existing CT scanning systems for the OC, can be removed, thereby saving costs. In addition, the operator can designate via the OC the conditions for overwriting data to the backup memories, and can also arrange the slots for the backup memories so as to insert an appropriate number of backup memories according to needs, which increases the flexibility of the scanning system using the backup memories so as to meet different backup requirements of raw data.

To be more specific, an embodiment of the present invention provides a method of transmitting raw data by the DAS in a CT scanning system, the CT scanning system being provided on the rotational part of the gantry with one or more raw data backup memories, the backup memories capable of being adopted by the DAS for storing a backup of the raw data, the method comprising: generating raw data as scanned; storing the generated raw data in the backup memory; transmitting the raw data to the OC in the CT scanning system; repeating the steps of generating, storing and transmitting the raw data in the case of unfinished scanning, until scanning is finished.

An embodiments of the present invention further provides a method of receiving raw data by the OC in a CT scanning system, the CT scanning system being provided on the rotational part of the gantry with one or more raw data backup memories, the backup memories capable of being adopted by the DAS of the CT scanning system for storing a backup of the raw data, and wherein the transmitting of received raw data comprises generating raw data as scanned, storing the generated rat data in the at least one backup memory, transmitting the raw data to an operation console in the CT scanning system, and repeating the generating, storing and transmitting of the raw data in the case of an unfinished scan, until the scan is finished. The method of receiving raw data by the operation console in the CT scanning system comprising: receiving raw data as scanned; detecting the received raw data; if no problem is found in the received raw data, continuing receiving in the case of unfinished scanning; if a problem is found in the received raw data, continuing receiving after recording an identifier of the raw data related to the problem in the case of unfinished scanning.

An embodiment of the present invention further provides a CT scanning system, the CT scanning system being provided on the rotational part of the gantry with one or more raw data backup memories, the backup memories capable of being adopted by a DAS in the CT scanning system for storing a backup of raw data.

BRIEF DESCRIPTION OF THE DRAWINGS

The present invention will be described in more detail below by referring to the following drawings, wherein the diagrammatic representation of the drawings is illustrative rather than restrictive, and the objective thereof is only to illuminate the principles of the present application, rather than to limit the present invention. Of the following drawings.

DETAILED DESCRIPTION OF THE INVENTION

Figure 5:
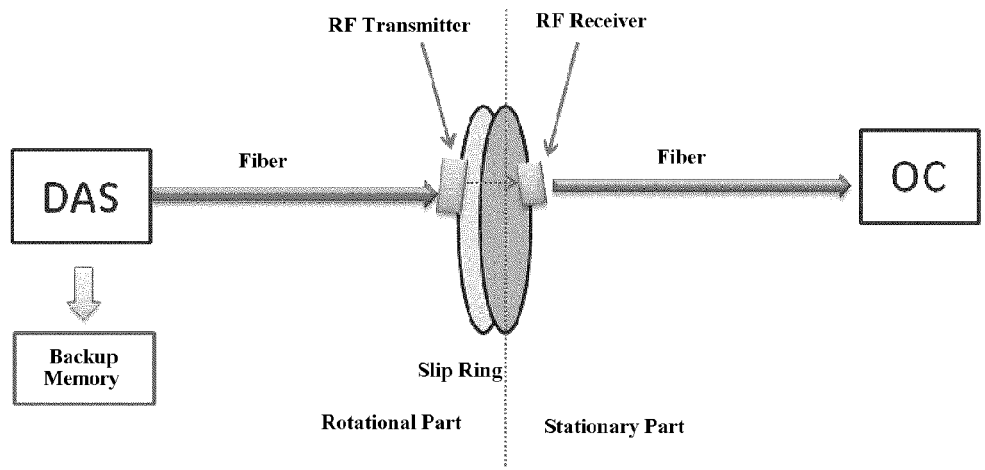
FIG. 5 is a block diagram showing the CT scanning system of an embodiment of the present invention.

FIG. 5 is a block diagram showing the CT scanning system of an embodiment of the present invention. For clarity and conciseness, the figure only shows the components that facilitate description of an embodiment of the present invention. In some embodiments of the present invention, the CT scanning system is provided on the rotation part of the gantry with one or more raw data backup memories, the backup memories are capable of being adopted by a DAS for storing a backup of raw data (persons skilled in the art understands that, the DAS can directly access the backup memories so as to access the backup of raw data, and can also indirectly access the backup memories so as to access the backup of raw data by means of, e.g., the Direct Memory Access (DMA) technology), such that the DAS in the CT scanning system of an embodiment of the present invention further stores the generated raw data into the backup memories before transmitting the generated raw data to the OC. In an embodiment of the present invention, the backup memories adopt non-volatile memories. In an embodiment of the present invention, the non-volatile memories can include but are not limited to one or more of storage cards, Flash, Solid State Disk (SSD). In an embodiment of the present invention, the backup memories adopt volatile memories, so as to make the speed of accessing data faster, but the stored backup of raw data will be lost after the rotational part is disconnected from the power supply. The storage space of the backup memories can be cyclically utilized, i.e., raw data is overwritten cyclically in the backup memories, and the previously stored data is covered automatically. In an embodiment of the present invention, the operator can designate via the OC the DAS's conditions for overwriting data by the backup memories. For example, one or more of the following conditions: time for overwriting data, period for overwriting data, overwriting can be started when a percentage of the occupied space of a backup memory accounts for the whole space, the data covered by overwriting is the earliest stored data or the least important stored data or the stored data that should be first covered according to other sorting, etc. Then, the OC transfers these conditions of overwriting data as designated by the operator to the DAS, so as to control the DAS's overwriting of data to the backup memories.

Figure 6:
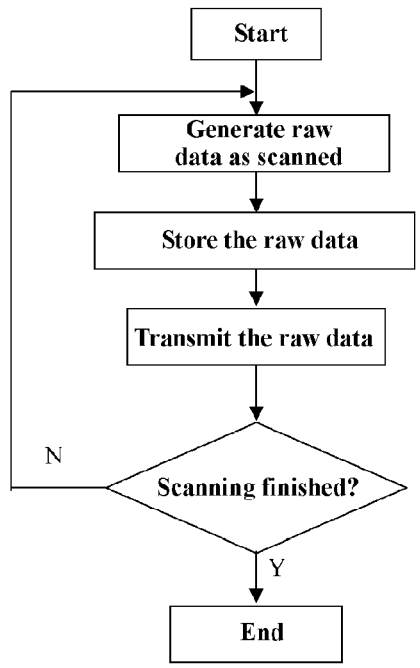
FIG. 6 is a flow diagram showing the method of transmitting raw data by the DAS of an embodiment of the present invention.

In an embodiment of the present invention, the rotational part of the scanning system of an embodiment of the present invention is provided with slots for the backup memories, such that the operator can insert an appropriate number of backup memories into the slots as needed FIG. 6 shows a method of transmitting raw data by the DAS in the CT scanning system of an embodiment of the present invention, the method comprising: the DAS generating raw data as scanned; storing the generated raw data in the backup memories; transmitting the raw data to the OC; repeating the steps of generating, storing and transmitting the raw data in the case of unfinished scanning, until scanning is finished.

In an embodiment of the present invention, the step of storing the generated raw data in the backup memories comprises the DAS directly accesses the backup memories so as to store the backup in the backup memories. The delay to the transmission of raw data, which is caused by the DAS directly accessing the backup memories so as to store raw data, is very small, so no impact is incurred to the transmission of raw data. However, when the real-time requirement of the raw data transmission is very high the DAS can be configured to indirectly access the backup memories via other components that are capable of directly accessing the backup memories in order to pursue a shorter delay. Hence, in another embodiment of the present invention, the step of storing the generated raw data in the backup memories is to instruct said other components to store the generated raw data in the backup memories. In this way, to enable raw data to be stored, the DAS only needs to transfer to said other components an instruction of storing raw data, subsequently raw data can be transmitted immediately by the DAS; now it can be deemed that the steps of storing and transmitting raw data are performed simultaneously, and almost no delay exists. In an embodiment of the present invention, said other components are one or more DMA components. Raw data is stored in the backup memories to form a backup of raw data, or called the backup raw data, so persons skilled in the art can understand that, the backup of raw data is also raw data. Obviously, persons skilled in the art will also understand that, the DAS stores raw data in the form of an electric signal, and transmits raw data in the form of a light signal.

In an embodiment of the present invention, the method as shown in FIG. 6 further comprises: if, upon completion of scanning, an instruction requiring retransmission of the backup raw data is received, obtaining one or more identifiers in the instruction for the raw data that is required to be retransmitted, reading from the backup memories the backup raw data corresponding to the identifier(s), and transmitting the read raw data to the OC. In an embodiment of the present invention, if there are a plurality of such identifiers in the instruction, the DAS's steps of reading and transmitting the backup raw data are carried out in turn per identifier. In an embodiment of the present invention, if there are a plurality of such identifiers in the instruction, the DAS reads the backup raw data corresponding to all identifiers at a time and then transmits these data to the OC. According to the teachings of the present invention, persons skilled in the art can readily conceive of other manners via which the DAS performs the reading and transmitting of the backup raw data, e.g., performs according to two identifiers at a time, which depends on such factors as the DAS's processing power, etc.

Figure 7:
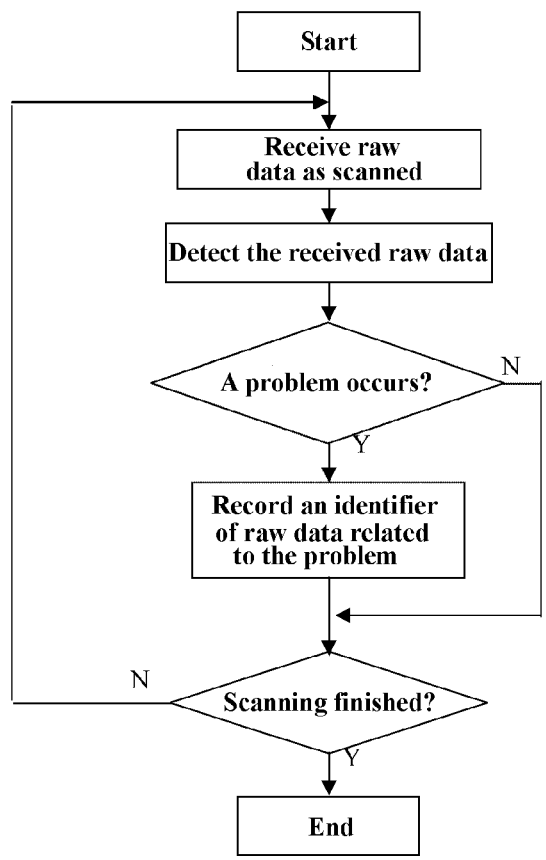
FIG. 7 is a flow diagram showing the method of receiving raw data by the OC of an embodiment of the present invention.

FIG. 7 shows a method of receiving raw data by the OC in the CT scanning system of an embodiment of the present invention, comprising: the OC receiving the raw data as scanned; the OC detects the received raw data, if it is not found by detection that the received raw data contains a problem, receiving is continued in the case of unfinished scanning; if it is found that the received raw data contains a problem, e.g., the received raw data has an error or some raw data is missed (e.g., a data package has an error or a data package is missed), identifier (e.g., a sequence number of the errant data package or a sequence number of the missing data package) of raw data related to the problem is recorded, so as to be convenient for further processing after scanning is completed, and then receiving is continued in the case of unfinished scanning In an embodiment of the present invention, the method as shown in FIG. 7 further comprises: after a problem is found in the received raw data, a step of deciding whether recording of the identifier of the raw data related to the problem is needed; if recording of the identifier is decided to be needed, the step of recording is performed, otherwise, receiving is continued in the case of unfinished scanning. In an embodiment of the present invention, if the OC is unable to remedy the problem via error correction code in the raw data related to the problem, recording of the identifier is decided to be needed; otherwise, it is not needed to record the identifier. In an embodiment of the present invention, if the OC is unable to remedy the problem via post-processing of the received raw data, recording of the identifier is decided to be needed, otherwise, it is not needed to record the identifier. In an embodiment of the present invention, conditions for deciding whether it is needed to record an identifier of raw data related to a problem can be designated by the operator via the OC.

In an embodiment of the present invention, the method as shown in FIG. 7 further comprises: after scanning is finished, the OC judges whether there is identifier(s) of raw data related to a problem which is/are recorded during a scanning process; if there is/are identifier(s), an instruction, requiring retransmission of the backup raw data corresponding to the identifier(s), is sent to the DAS, the instruction carrying the identifier(s). After receiving the above instruction, the DAS transmits the backup raw data corresponding to the identifier(s), as stated above. In another embodiment of the present invention, if there is/are the identifier(s) recorded, the identifier(s) is/are adopted by the operator for manually copying the backup raw data corresponding to the identifier(s) in the backup memory to the OC. In addition, during the debugging or system warm-up scanning, if there is/are the identifier(s) recorded, it is not necessary to retransmit or copy the backup raw data to the OC, so in another embodiment of the present invention, the fact whether there is the recorded identifier(s) is only used by the OC or the operator to judge whether the system operates abnormally.

In an embodiment of the present invention, the method as shown in FIG. 7 further comprises recording the problem and the time of that moment while recording the identifier of raw data related to the problem. The records related to the problem can be used for analysis of system performance.

Figure 1:
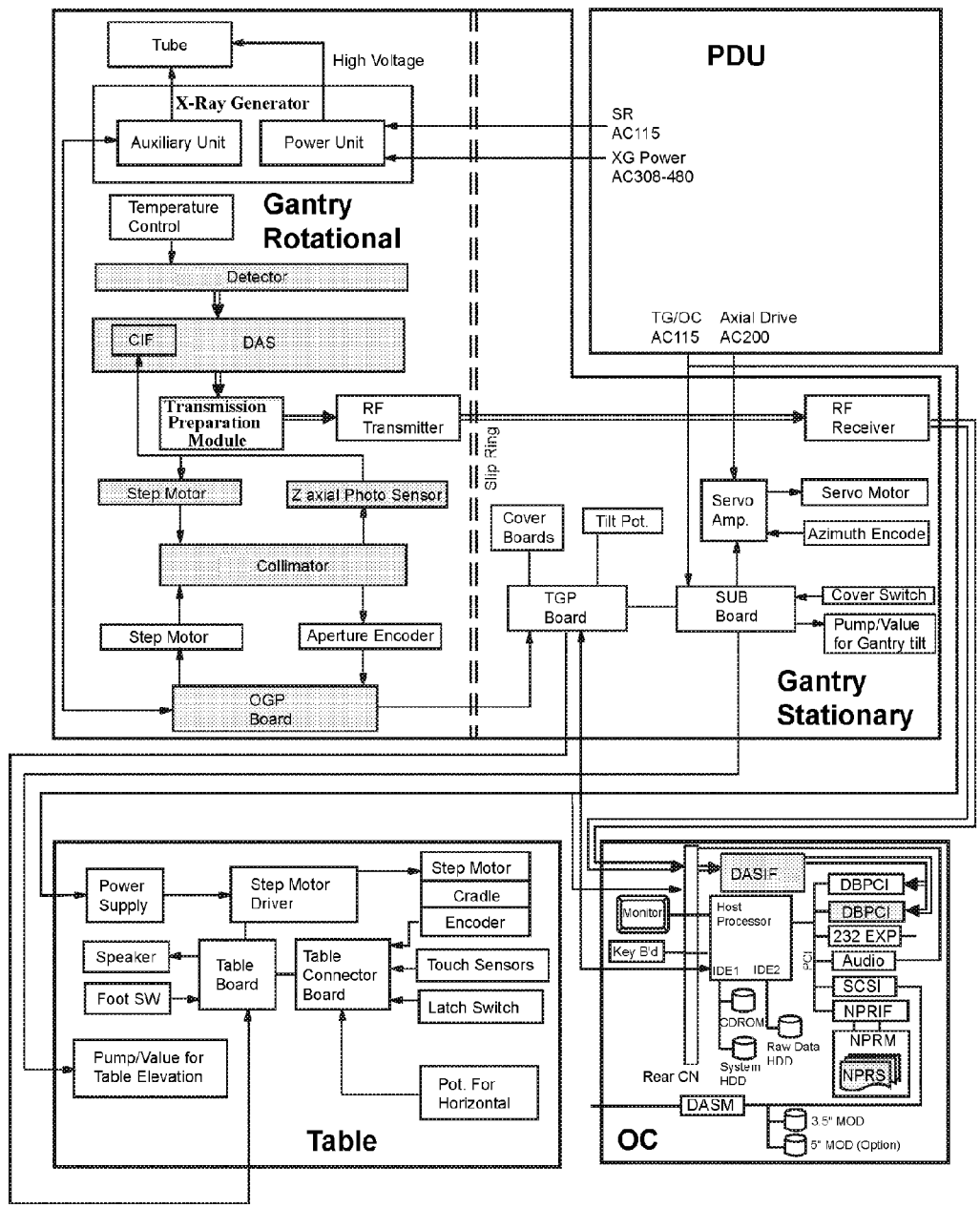
FIG. 1 is a block diagram of a CT scanning system.
Figure 2:
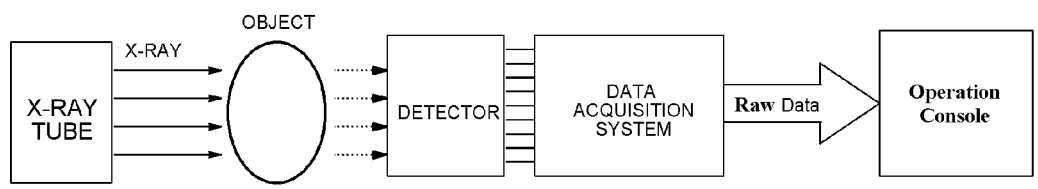
FIG. 2 is a block diagram of an X-ray tube and a data detection-acquisition part.
Figure 3:
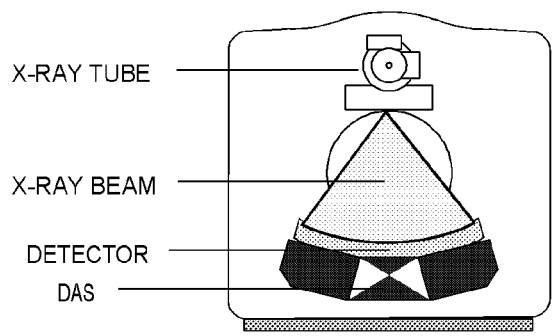
FIG. 3 is a schematic diagram of an X-ray tube and a data detection-acquisition part.
Figure 4:
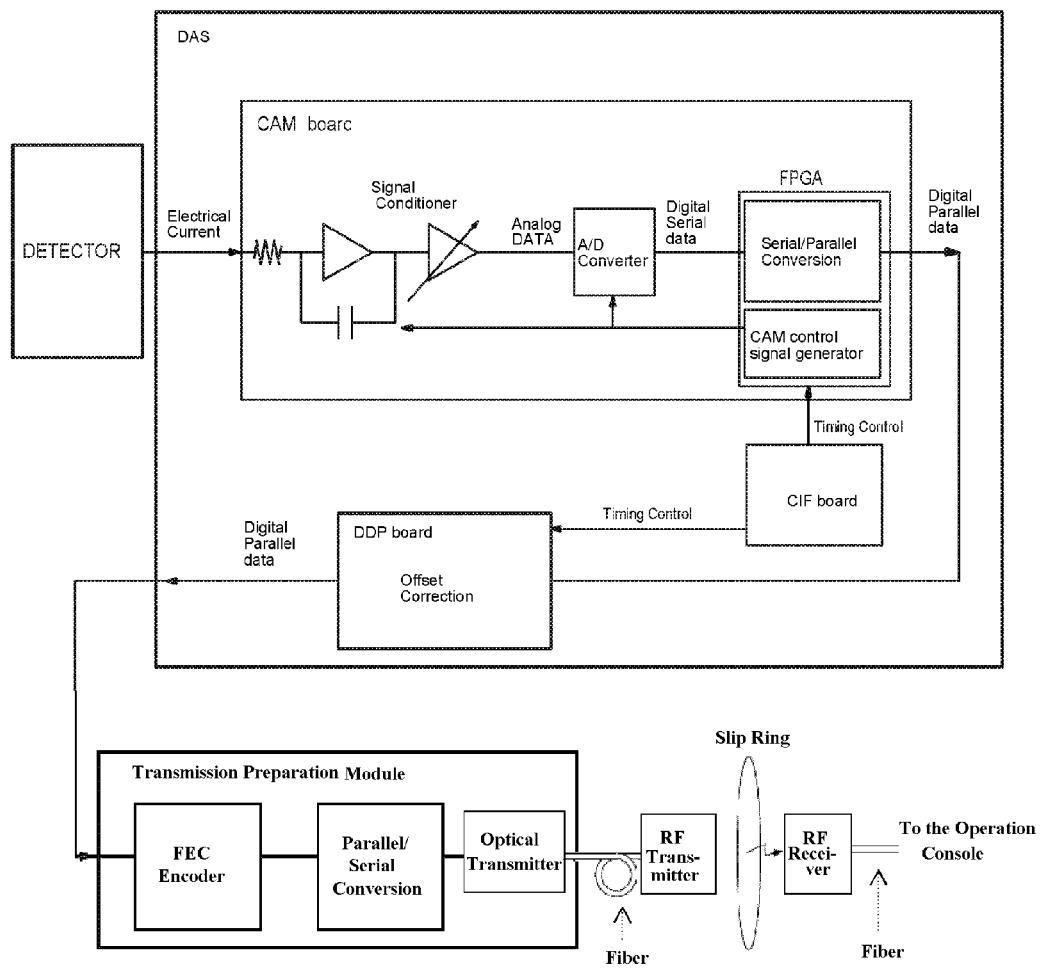
FIG. 4 is a block diagram of a DAS.

As mentioned in the "BACKGROUND OF THE INVENTION", the link on the slip ring for transmitting raw data is different from the link on the slip ring for communication between the OGP board and the OC, and other parts of the path between the OGP board and the OC are also different from the transmitting path of raw data (see FIG. 1), whereby the inventors conceives that, e.g., in the case that a failure occurs in the transmitting path of raw data or debugging is conducted, the retransmitted raw data can also be sent by the OGP board to the OC by means of the path between the OGP board and the OC. Hence, in an embodiment of the present invention, the OGP board is configured to be capable of reading a backup of raw data in the backup memory and performing an instruction requiring retransmission of the backup raw data. The method as shown in FIG. 7 further comprises: after scanning is finished, an OC judges whether there is/are identifier(s) of raw data related to problem(s), which is/are recorded during a scanning process; if there is/are identifier(s), an instruction, requiring retransmission of the backup raw data corresponding to the identifier(s), is sent to the OGP board, the instruction carrying the identifier(s).

The backup memory is provided on the rotational part of the gantry, so that during the scanning, when the OC finds occasional problems in the received raw data and these problems cannot be corrected by error correction codes, the OC can issue an instruction to retransmit from the backup memory the correct backup of data related to the problems, instead of remedying these occasional data problems by post-processing as the prior art does. In most cases, when the backup of raw data is retransmitted, unexpected factors (e.g., voltage mutation or mobile phone signals) that lead to the problems occurring in the initially received data do not exist any more, so the retransmitted data backup can be correctly sent to the OC. Even if, in very few cases, the data backup received by the OC is still incorrect, it is only needed to simply issue an instruction for retransmission again. After receiving the correct backup of data, the OC can use the correct backup for image reconstruction, so as to ensure high quality of reconstructed image. In addition, even if there are relatively more problems found in the received data by the OC, these problems can also be remedied by receiving the correct backup from the backup memory, avoiding abortion of the scan as existing scanning systems do when the number of problems reach a threshold value, thereby avoiding re-scanning the object.

In the case of a serious failure, such as the transmitting path of raw data between the DAS and the OC is damaged, soft/hardware invalidation on the OC, or power down of the OC, the data transmission between the DAS and the OC will be interrupted. In this case, although some data that is finally transmitted prior to interruption of data transmitting is missed due to the serious failures, once the serious failures are repaired, the OC can issue an instruction to retransmit the backup of the missed data from the backup memory or the operator can manually copy the backup of the missed data from the backup memory to the OC to restore the missed data, and it is not necessary to start data transmission from the beginning.

In addition, although the interruption of data transmission occurs, it is not necessary to abort scanning as the prior art does, because the scanned data can be stored in the backup memory, so as to ensure that scanning can be continued without concerned that data is missed due to transmission interruption. This is particularly beneficial to the areas or situations in which power supply is not stable. Even if the power supply is not sufficient to keep the normal operation of the OC, as long as the power supply for the normal operation of the CT gantry and the DAS is maintained normal, the scanning can continue.

Figure 8:
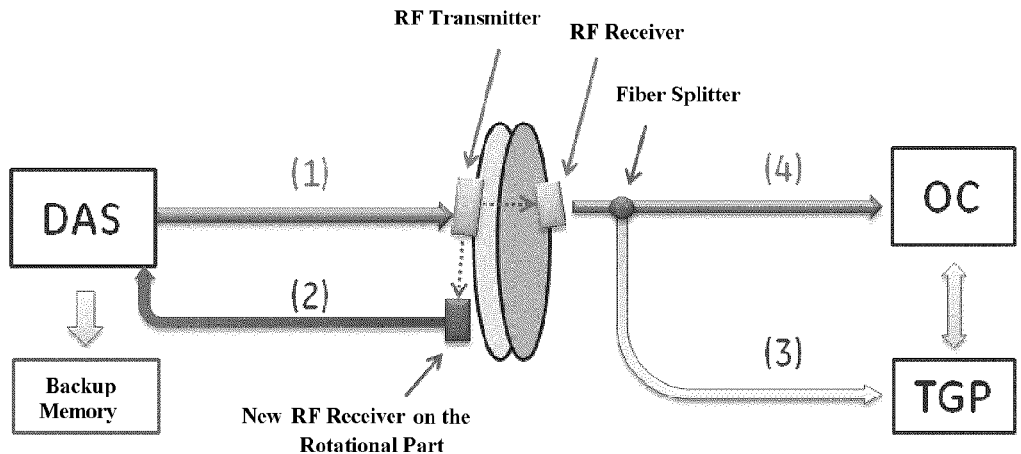
FIG. 8 is a schematic diagram of data echoplex and signal splitting of an embodiment of the present invention.
Figure 9:
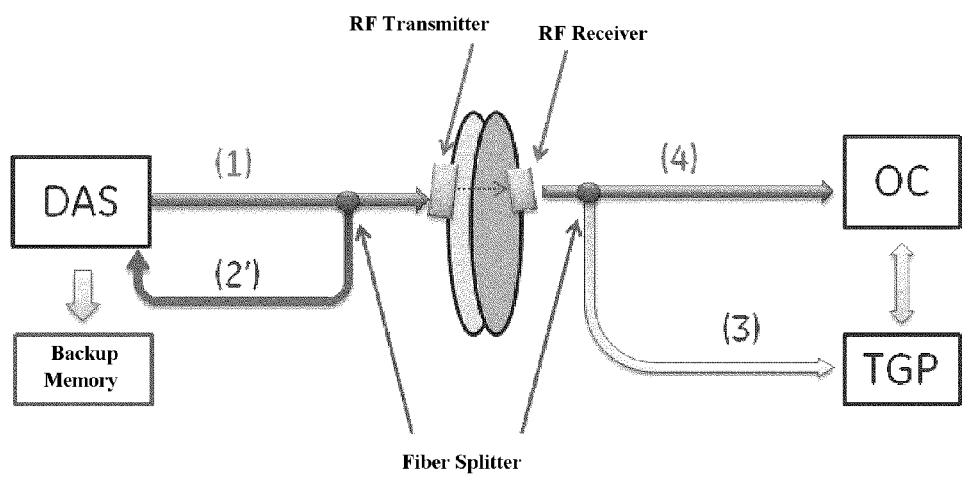
FIG. 9 is a schematic diagram of another data echoplex and signal splitting of an embodiment of the present invention.

In another embodiment of the present invention, the DAS can further generate a warning message favorable for failure detection. To be more specific, a data echoplex component is provided on the rotational part, the DAS is configured to be able to receive, via the echoplex component, the raw data as transmitted out, the DAS detects the received raw data, and if it is found by detection that the received raw data encounters a problem, a warning message reporting a problems has been found is sent to the OC. In an embodiment of the present invention, the DAS detects the received raw data by comparing the received raw data with the corresponding backup stored in the backup memory (if the comparing result is not consistent, it naturally indicates that the received raw data contains a problem). In another embodiment of the present invention, the DAS utilizes an error correction code in the received raw data to detect the received data. According to the teachings of the present invention, persons skilled in the art can readily conceive of other manners of detecting the received raw data. Source address fields in the header of the warning message can make the OC aware that the warning message is issued from the DAS. The OC records the warning message when receiving the warning message, so as to facilitate the subsequent failure detection (described below). The OC can also record the time it received the warning message at the same time to facilitate the subsequent analysis of system performance (described below). In an embodiment of the present invention, as shown in FIG. 8, the echoplex component is a RF receiver mounted on the rotational part and a fiber between the RF receiver and the DAS (represented by reference sign (2) in FIG. 8). In another embodiment of the present invention, as shown in FIG. 9, the echoplex component is a fiber splitter on the rotational part, which is mounted on the fiber from the DAS to the RF transmitter, and a fiber between the fiber splitter and the DAS (represented by reference sign (2') in FIG. 9). According to the teachings of some embodiments of the present invention, persons skilled in the art can readily conceive of other ways to realize the echoplex component. Persons skilled in the art can also understand that, the above method of sending the warning message by the DAS can be used alone or in combination with the method as shown in FIG. 6.

In practical application of the CT scanning system, the segment (4) of fiber from the RF receiver on the stationary part of the gantry to the OC often encounters failures, because the distance from the RF receiver to the OC is relatively far (generally about 20-100 meters), such that thin and fragile fibers tend to suffer damages from exoteric strikes or pressure. In order to quickly judge whether this segment of fiber encounters a failure, in an embodiment of the present invention, a fiber splitter that follows closely the RF receiver on the stationary part is provided on the fiber connected to the OC, a fiber is provided between the fiber splitter and the TGP board (represented by reference sign (3) in FIGS. 8 and 9), and the TGP board is configured to be also capable of receiving light signal raw data that is split from the fiber connected to the OC. The TGP board can detect the received raw data, and once a problem is found, send to the DAS a warning message reporting that a problem is found. Source address fields in the header of the warning message can make the OC aware that the warning message is issued from the TGP board. Similarly, the OC records the warning message when receiving the warning message, so as to facilitate the subsequent failure detection (described below); the OC can also record the time it received the warning message at the same time, so as to facilitate the subsequent analysis of system performance (described below). It shall be noted that, although the TGP board and the fiber splitter are also connected by a fiber, the distance of fiber segment (3) is short, usually less than 1 meter, so it is deemed that fiber segment (3) has a very low probability of suffering from exoteric damages. That is, fiber segment (3) is less likely to be damaged by exoteric strikes or pressure than fiber segment (4). The cable between the TGP board and the OC is a common net wire of local area network, which is much stronger than the fiber, so it is also deemed that the cable is less likely to be susceptible to damage than fiber segment (4). Persons skilled in the art will also understand that, the above method of sending the warning message by the TGP board can be used alone or in combination with the method of sending the warning message by the DAS.

In the case of existence of failures, the OC can check the storage of warning messages to facilitate failure detection. For example, assuming that the DAS and the TGP board both can send a warning message, after the DAS transmit raw data to the OC, if neither the DAS nor the TGP board send a warning message, and the OC finds a problem in the received data, which shows that the fiber splitter connected to the TGP board and the components in front of it in the transmitting path of raw data do not contain a failure, and the segment (4) of fiber may suffer from a failure; if the DAS does not send a warning message, and the TGP board sends a warning message, which shows that the echoplex component and the components in front of it in the transmitting path of raw data do not contain a failure, the components after it may suffer from a failure; if the DAS sends a warning message, it can be judged that the segment (1) may suffer from a failure. Certainly, according to the teachings of the present invention, persons skilled in the art can design other methods of performing failure detection. As such, persons skilled in the art appreciate that, even if only the DAS can send a warning message, it is also favorable for failure detection. For example, if during the transmitting of data the DAS does not send a warning message, this will demonstrate that the echoplex component and the components in front of it in the transmitting path of raw data do not contain a failure.

If the warning message not only reports to the DAS that a data problem has been found, but also contains more information, the warning message can also be used for analysis of system performance. Hence, in an embodiment of the present invention, the warning message further comprises operating information of the DAS or the TGP board when the problem is found, e.g., time for which the DAS or the TGP board has been operated, status information in a register on the DAS or the TGP board, and load level of a processor on the DAS or the TGP board, when the problem is found. The OC can combine the operating information in the recorded warning message and the time it received the warning message together to perform a system performance analysis. For example, which period of time is a period for which problems frequently occur, which path segment is a path segment in which problems frequently occur, what period of operation for the DAS or the TGP board results in problems more easily occurring, at what load levels of the processors on the DAS or the TGP board results in problems more easily occurring, etc. The OC can also combine the records of warning messages during the scanning and the records related to the problems as mentioned above together to perform analysis of system performance, so as to work out more specific system performance. For example, which period of time is a period for which what kinds of problems frequently occur, which path segment is a path segment in which what kinds of problems frequently occur, what kinds of problems more frequently occur in relation to how long the DAS or the TGP board has been operated, what kinds of problems more frequently occur in relation to the load level of the processor on the DAS or the TGP board, etc. Persons skilled in the art can understand that, the records related to the problems as mentioned above can also be used alone for analysis of system performance.

In an embodiment of the present invention, the DAS can also detect the backup memory before transmitting data, so as to determine whether the backup memory per se suffers from failures. In an embodiment of the present invention, this detection refers to the DAS writing some data into the backup memory, then reading these data from the backup memory, and comparing the data as written-in and the data as read. If a comparing result is consistent, it can be determined that the backup memory operates normally; otherwise, it is judged that the backup memory encountered a failure. According to the teachings of the present invention, persons skilled in the art can readily conceive of other manners of detecting the backup memory.

In an embodiment, the echoplex component is a fiber splitter on the rotational part which is mounted on the fiber from the data acquisition system to the RF transmitter of the CT scanning system, and a fiber between the fiber splitter and the data acquisition system.

In an embodiment, the warning message comprises operating information of the data acquisition system when the problem is found.

In an embodiment, the operating information refers to time for which the data acquisition system has been operated, status information in a register on the data acquisition system, and load level of a processor on the data acquisition system, when the problem is found.

In an embodiment, the data acquisition system can also detect the backup memory before transmitting the raw data.

In an embodiment, the detecting of the backup memory refers to that the data acquisition system writes some data into the backup memory, then reads these data from the backup memory, and compares the data as written-in and the data as read; if a comparing result is consistent, it can be determined that the backup memory operates normally; otherwise, it is judged that the backup memory encounters a failure.

In an embodiment, if the operation console is unable to remedy the problem via post-processing the received raw data, recording of the identifier is decided to be needed; otherwise, it is not needed to record the identifier.

In an embodiment, the conditions for deciding whether recording of an identifier of raw data related to a problem can be designated by the operator via the operation console.

In an embodiment, if there is the identifier(s) as recorded, the identifier(s) is/are adopted by an operator for manually copying the backup raw data corresponding to the identifier in the backup memory to the operation console.

Although the present invention has been described by referring to specific embodiments, the description generally intends to illuminate the inventive concept, and shall not be construed as limiting the inventive scope, which shall be defined by the attached claims. Certainly, persons skilled in the art will also appreciate that, without departing from the basic characteristics of the present invention, the present invention can also be performed in other manners that are different from those manners as specifically stated herein. Therefore, the embodiments as presented herein are deemed to be illustrative rather than restrictive in all aspects, and all changes that fall within the meaning and equivalent range of the attached claims are intend to be embraced therein.

What is claimed is:

1. A method of transmitting raw data by a data acquisition system in a CT scanning system, wherein the CT scanning system comprises a rotational part of a gantry with at least one raw data backup memory, and wherein the data acquisition system is configured to adopt the at least one backup memory for storing a backup of the raw data, the method comprising:
   generating the raw data as scanned;
   storing the generated raw data in the at least one backup memory;
   transmitting the raw data to an operation console in the CT scanning system until the scan is finished,
   determining whether an error in transmitting of the raw data has occurred,
   obtaining at least one identifier in the instruction associated with said error;
   reading from the at least one backup memory, the backup raw data corresponding to the at least one identifier; and
   transmitting the read raw data to the operation console.

2. The method according to claim 1, wherein storing the generated raw data in the at least one backup memory comprises the data acquisition system directly accessing the at least one backup memory to store the generated raw data in the at least one backup memory.

3. The method according to claim 1, wherein the data acquisition system is configured to indirectly access the backup memory via other components configured to directly access the backup memory, and storing the generated raw data in the at least one backup memory comprises instructing the other components to store the generated raw data in the at least one backup memory.

4. The method according to claim 3, wherein the other components are at least one Direct Memory Access (DMA) components.

5. The method according to claim 1, wherein, if there are a plurality of identifiers in the instruction, reading and transmitting the backup raw data are carried out in turn per identifier.

6. The method according to claim 1, wherein, if there are a plurality of identifiers in the instruction, the backup raw data corresponding to all identifiers is read at a time and transmitted to the operation console.

7. The method according to claim 1, wherein the CT scanning system further comprises a data echoplex component located on the rotational part of the gantry, wherein the data acquisition system is configured to receive, via an echoplex component, the raw data as transmitted out, the method further comprising:
   detecting by the data acquisition system the received raw data; and
   if it is detected that the received raw data encountered a problem, sending to the operation console a warning message reporting a problem has been found.

8. The method according to claim 7, wherein the data acquisition system detects the received raw data by comparing the received raw data with the corresponding backup of the raw data stored in the backup memory.

9. The method according to claim 7, wherein the data acquisition system utilizes error correction code in the received raw data to detect the received raw data.

10. The method according to claim 7, wherein the echoplex component is a RF receiver mounted on the rotational part and a fiber between the RF receiver and the data acquisition system.

11. A method of receiving raw data by an operation console in a CT scanning system, wherein the CT scanning system comprises a rotational part of a gantry with at least one raw data backup memory, a data acquisition system configured to store a backup of the raw data in the at least one backup memory, and a processor configured to generate the raw data as scanned, store the generated raw data in the at least one backup memory, transmit the raw data to the operation console in the CT scanning system, and repeat the generating, storing and transmitting of the raw data in the case of an unfinished scan, until the scan is finished, the method comprising:
   receiving the raw data as scanned;
   detecting the received raw data; and
   if a problem is not found in the received raw data and a scan is not finished, continuing receiving raw data; or
   if a problem is found in the received raw data and the scan is not finished, continuing receiving raw data after recording an identifier of the raw data related to the problem.

12. The method according to claim 11, further comprising, after a problem is found in the received raw data, deciding whether recording of the identifier of the raw data related to the problem is needed, if recording of the identifier is decided to be needed, recording is performed, and if recording of the identifier is decided not to be needed, receiving raw data is continued in the case of the unfinished scan.

13. The method according to claim 12, wherein, if the operation console is unable to remedy the problem via an error correction code in the received raw data related to the problem or via post-processing of the received raw data, recording of the identifier is decided to be required, if the operation console is able to remedy the problem by way of the error correction code in the received raw data related to the problem or via post-processing of the received raw data, recording of the identifier is not required.

14. The method according to claim 11, further comprising:
   after the scan is finished, judging, by the operation console, whether there is/are identifier(s) recorded during the scan; and
   if there is identifier(s) recorded during the scan, an instruction requiring retransmission of the backup of the raw data corresponding to the identifier(s) and carrying the identifier(s) is sent to the data acquisition system.

15. The method according to claim 11, wherein an OGP board in the CT scanning system is configured to read the backup of raw data in the at least one backup memory and to perform an instruction requiring retransmission of the backup raw data, the method further comprising:
   after the scan is finished, judging, by the operation console, whether there is identifier(s) recorded during the scan process; if there is identifier(s) recorded during the scan process, an instruction requiring retransmission of the backup of the raw data corresponding to the identifier(s) and carrying the identifier(s), is sent to the OGP board.

16. A CT scanning system, comprising:
a rotational part of a gantry with at least one raw data backup memory, the rotational part comprising a data echoplex component; and
a data acquisition system configured to:
receive, via the echoplex component, the raw data; and
store a backup of the raw data in the at least one backup memory, wherein the data acquisition system cyclically overwrites data in the at least one backup memory.

17. The system according to claim 16, wherein the data acquisition system directly accesses the at least one backup memory or indirectly accesses the at least one backup memory via other components configured to directly access the at least one backup memory.

18. The system according to claim 16, where the at least one backup memory comprises at least one non-volatile memory or at least one volatile memory.

19. The system according to claim 16, wherein the rotational part is provided with at least one slots for the at least one backup memory, such that an appropriate number of backup memories can be inserted into the at least one slot as required.

\* \* \* \* \*

UNITED STATES PATENT AND TRADEMARK OFFICE
CERTIFICATE OF CORRECTION

| | | |
|---|---|---|
| PATENT NO. | : 9,342,398 B2 | Page 1 of 1 |
| APPLICATION NO. | : 14/166992 | |
| DATED | : May 17, 2016 | |
| INVENTOR(S) | : Li et al. | |

It is certified that error appears in the above-identified patent and that said Letters Patent is hereby corrected as shown below:

In the specification

In Column 3, Line 1, delete "object me be" and insert -- object may be --, therefor.

In Column 6, Line 44, delete "scanning" and insert -- scanning. --, therefor.

Signed and Sealed this
Twenty-third Day of August, 2016

Michelle K. Lee
*Director of the United States Patent and Trademark Office*